US011083427B2

(12) United States Patent
Pruyne

(10) Patent No.: US 11,083,427 B2
(45) Date of Patent: Aug. 10, 2021

(54) SYSTEM AND METHOD TO SECURE DEVICE

(71) Applicant: CARESTREAM HEALTH, INC., Rochester, NY (US)

(72) Inventor: Adam D. Pruyne, Webster, NY (US)

(73) Assignee: Carestream Health, Inc., Rochester, NY (US)

( * ) Notice: Subject to any disclaimer, the term of this patent is extended or adjusted under 35 U.S.C. 154(b) by 156 days.

(21) Appl. No.: 16/672,567

(22) Filed: Nov. 4, 2019

(65) Prior Publication Data

US 2020/0155092 A1 May 21, 2020

Related U.S. Application Data

(60) Provisional application No. 62/769,204, filed on Nov. 19, 2018.

(51) Int. Cl.
*A61B 6/00* (2006.01)
(52) U.S. Cl.
CPC ............ *A61B 6/447* (2013.01); *A61B 6/4405* (2013.01); *A61B 6/4476* (2013.01); *A61B 2560/0437* (2013.01)

(58) Field of Classification Search
CPC .. A61B 6/06; A61B 6/4035; G01N 2223/313; G01N 23/083; G21K 1/10
See application file for complete search history.

(56) References Cited

U.S. PATENT DOCUMENTS 8,876,379 B2 * 11/2014 DiRisio ................. A61B 6/447
378/198

* cited by examiner

*Primary Examiner* — Dani Fox

(57) ABSTRACT

A mobile radiography system includes a wheeled transport frame and a telescoping vertical column mounted on the transport frame. The vertical column includes a stationary base section and a vertically movable upper section coupled to the base section. A cap is positioned in a nest at the top of the movable upper section whereby a counterweight in the movable upper section displaces the cap when the counterweight is extended through the nest and replaces the cap in the nest when the counterweight is retracted into the movable upper section. A padded section of the nest and the counterweight prevents impact noise when the cap contacts the nest or the counterweight. Magnets are used to hold the cap and the nest together in alignment when they are adjacent.

16 Claims, 9 Drawing Sheets

SYSTEM AND METHOD TO SECURE DEVICE

CROSS REFERENCE TO RELATED APPLICATIONS

This application claims priority to U.S. Patent Application Ser. No. 62/769,204, filed Nov. 19, 2018, in the name of Adam D. Pruyne, and entitled SYSTEM AND METHOD TO SECURE DEVICE, which is hereby incorporated by reference herein in its entirety.

This application is related in certain respects to U.S. Pat. No. 8,876,379 B2, filed Apr. 11, 2011, in the name of Dirisio et al., and entitled COLLAPSIBLE COLUMN MOVEMENT APPARATUS FOR MOBILE X-RAY DEVICE, which is hereby incorporated by reference herein in its entirety.

BACKGROUND OF THE INVENTION

The invention relates generally to the field of medical imaging, and in particular to portable radiographic imaging apparatus. More specifically, the invention relates to a mobile radiography apparatus including improved operational features.

Mobile carts are employed in medical facilities to move medical equipment between locations. One type of mobile cart includes an x-ray source used to capture digital x-ray images in a digital radiographic detector. Mobile x-ray apparatus are of particular value in intensive care apparatus (ICU) and other environments where timely acquisition of a radiographic image is important. Because portable carts can be wheeled around the ICU or other area and brought directly to the patient's bedside, a portable x-ray imaging apparatus allows an attending physician or clinician to have recent information on the condition of a patient and helps to reduce the risks entailed in moving patients to stationary equipment in the radiological facility.

The discussion above is merely provided for general background information and is not intended to be used as an aid in determining the scope of the claimed subject matter.

BRIEF DESCRIPTION OF THE INVENTION

A mobile radiography system includes a wheeled transport frame and a telescoping vertical column mounted on the transport frame. The vertical column includes a stationary base section and a vertically movable upper section coupled to the base section. A cap is positioned in a nest at the top of the movable upper section whereby a counterweight displaces the cap when the counterweight is extended past the top of the movable upper section, and whereby the counterweight replaces the cap when the counterweight is retracted into the movable upper section. A padded section on the top of the counterweight prevents impact noise when the counterweight contacts the cap. A padded section of the nest prevents impact noise when the cap contacts the nest. Magnets are used to hold the cap and the nest together when they are adjacent. An advantage that may be realized in the practice of some disclosed embodiments of the mobile radiography system is quieter operation.

In one embodiment, a mobile radiography system includes a wheeled transport frame for transporting the system. A telescoping vertical column is mounted on the transport frame. The vertical column includes a stationary vertical base section and a vertically movable upper section coupled to the base section and movable relative to the base section. A nest with a magnet is attached to a top of the movable upper section and a cap with a magnet is held against the nest by the magnets in the cap and the nest. The cap is configured to be displaced from the nest by a counterweight extending from the movable upper section. The cap is also configured to be replaced in the nest when the counterweight is retracted into the movable upper section.

In another embodiment, a mobile radiography system includes a transport frame having wheels for transporting the system. A telescoping vertical column is mounted on the transport frame. The vertical column includes a stationary base section and a vertically movable upper section. A counterweight is disposed within the movable upper section. A nest is attached to a top of the movable upper section and a cap is seated in the nest. The cap is configured to be displaced from the nest when a counterweight is extended through the nest, and to be replaced in the nest when the counterweight is retracted.

The cap is a feature configured to reduce noise. Inherently, there are many contact points that slide against each other in a telescoping column design. The fit between these parts needs to be loose to avoid binding. As a result, the parts may rattle whenever the system is jarred or is in transport. The present invention mitigates these noises effectively due to several design improvements. The only contact the counterweight has with the cap is when the counterweight lifts the cap off its nest. To mitigate the noise associated with this engagement, a polyurethane padding, preferably PORON® made by Rogers Corporation, for example, has been incorporated at the contact surfaces. PORON® is a material that reacts differently based on speed at impact. It absorbs the energy of the engagement and therefore minimizes noise.

To mitigate noise associated with loose fitting parts during transit, magnets have been incorporated between the cap and its nest to hold the cap firmly against a polyurethane padding during transport. The only contact the cap has with the nest is when the cap is seated in the nest. To mitigate the noise associated with this engagement, a polyurethane padding has been incorporated in the nest at the contact points between the cap and the nest. The magnetic force between the cap and the nest ensures that enough force is provided to stabilize the cap in the nest. Additionally, the magnetic attraction helps to kinematically locate the cap properly so that it always engages the counter weight in the same location to minimize the possibility of scraping during engagement of the cap to the counterweight.

The summary descriptions above are not meant to describe individual separate embodiments whose elements are not interchangeable. In fact, many of the elements described as related to a particular embodiment can be used together with, and possibly interchanged with, elements of other described embodiments. Many changes and modifications may be made within the scope of the present invention without departing from the spirit thereof, and the invention includes all such modifications.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings below are intended to be drawn neither to any precise scale with respect to relative size, angular relationship, relative position, or timing relationship, nor to any combinational relationship with respect to interchangeability, substitution, or representation of a required implementation, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Figure 1:
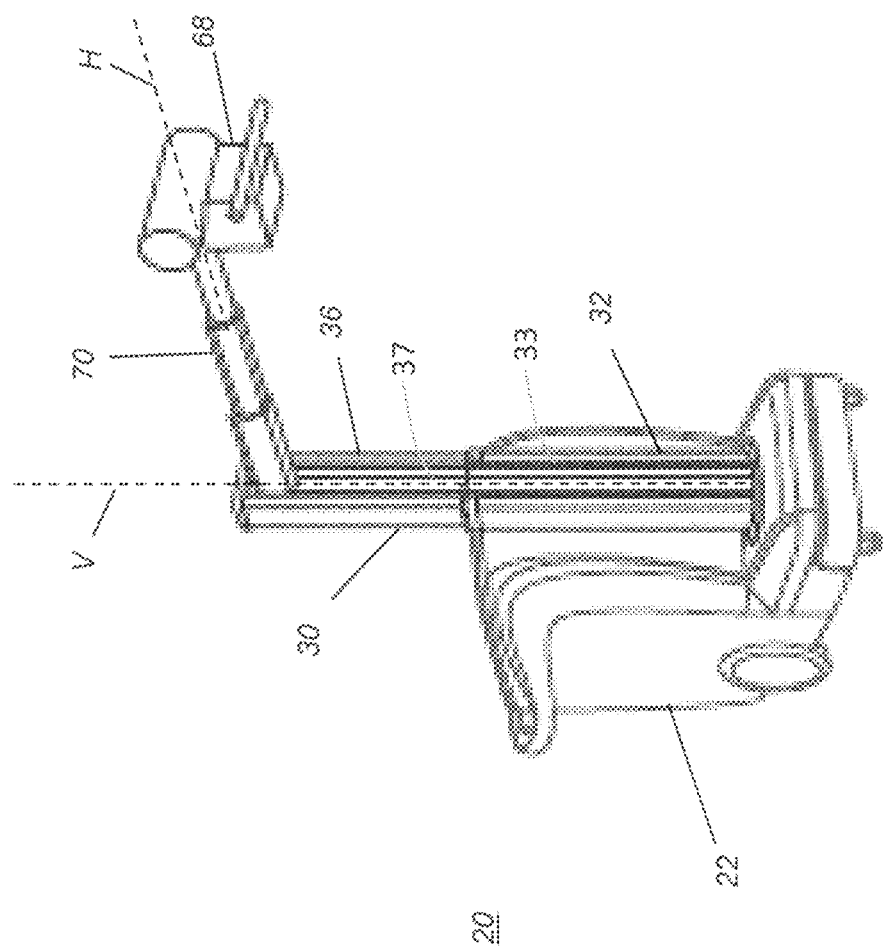
FIG. 1 is a perspective view of a mobile radiography apparatus.
Figure 2B:
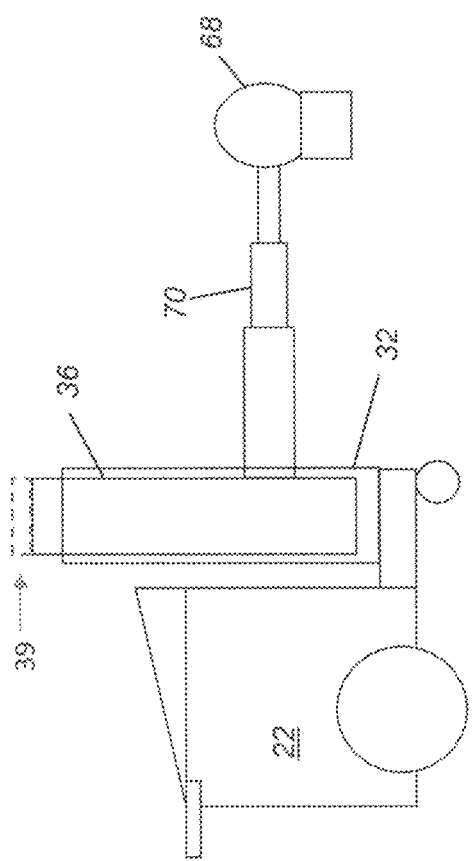
FIGS. 2A-2B are schematic side views of the mobile radiography apparatus of FIG. 1.
Figure 2A:
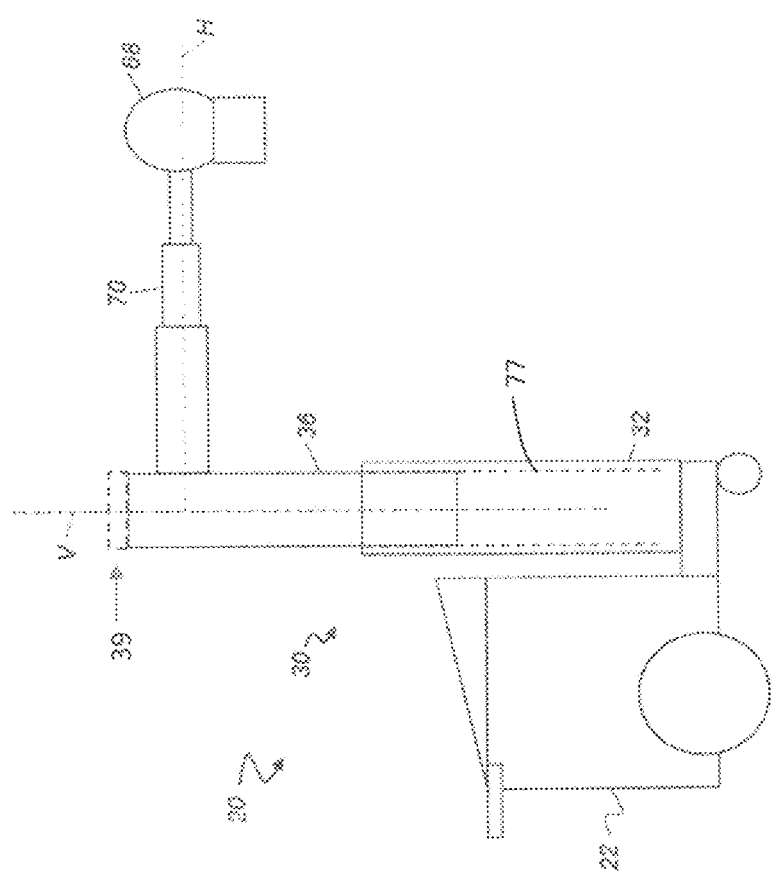

With reference to FIG. 1 and FIGS. 2A-2B, a mobile radiography apparatus 20 includes a telescoping boom 70 coupled to a telescoping, sectioned vertical column 30 according to one embodiment. An x-ray tube head 68 is in position for imaging, extended outward and supported by boom 70, along a horizontal axis H that may be perpendicular, or slightly angled, relative to the vertical axis V. The mobile radiography apparatus 20 has a wheeled transport frame 22. Telescoping sectioned vertical column 30 is mounted on frame 22 parallel to the vertical axis V and has a vertically stationary base section 32 that seats against the frame 22. At least one movable section 36 is vertically translatable within the stationary base section 32 to extend along the vertical axis V, so that boom 70 and x-ray tube head 68 can be set to a suitable height over a range of possible height settings.

Embodiments of the present invention use a boom transport mechanism that cooperates mechanically with the telescoping, sectioned vertical column 30 to allow displacement of the boom 70 over a wide range of height settings as described herein. An operator can easily adjust a height of the boom 70 with the weight of column 30 and boom 70 components mechanically balanced so that a substantially uniform amount of effort is needed for height adjustment of the boom 70 to any level within its height range. As shown in FIG. 2A, stationary base section 32 may include a hollow cavity or shaft 77 allowing movable section 36 to travel vertically therethrough. As shown in FIG. 1, stationary base section 32 may include a vertical slit or opening 33 allowing the boom 70 to travel vertically therethrough along a track 37 in the movable section 36. As shown in FIG. 2A, the boom 70 may be raised to a height near the top of movable section 36 while movable section 36 is extended vertically within shaft 77 of stationary base section 32. As shown in FIG. 2B, the boom 70 may be lowered to a height closer to a bottom of movable section 36 while movable section 36 is retracted vertically within the shaft 77 of stationary base section 32.

Figure 3B:
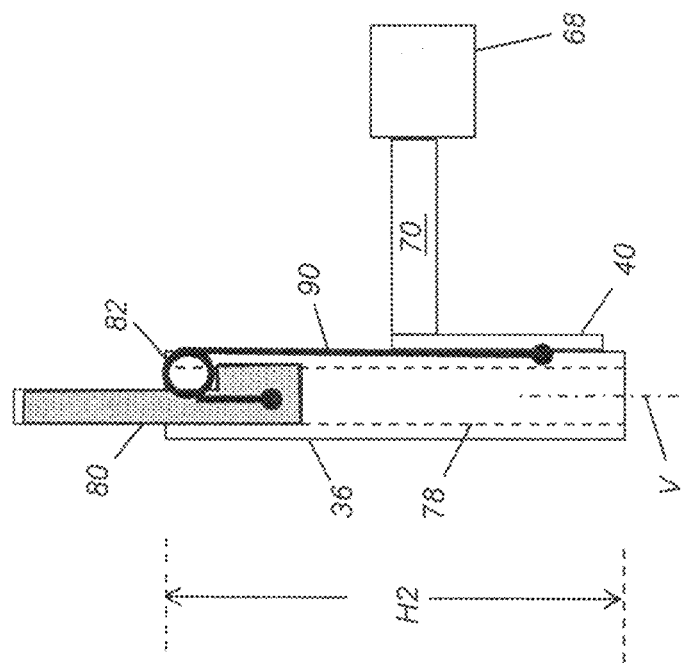
FIGS. 3A and 3B show schematically the movable upper section and the boom using a counterweight housed within the movable upper section and which may extend above a top of the movable upper section when the boom is in a lowered position.
Figure 3A:
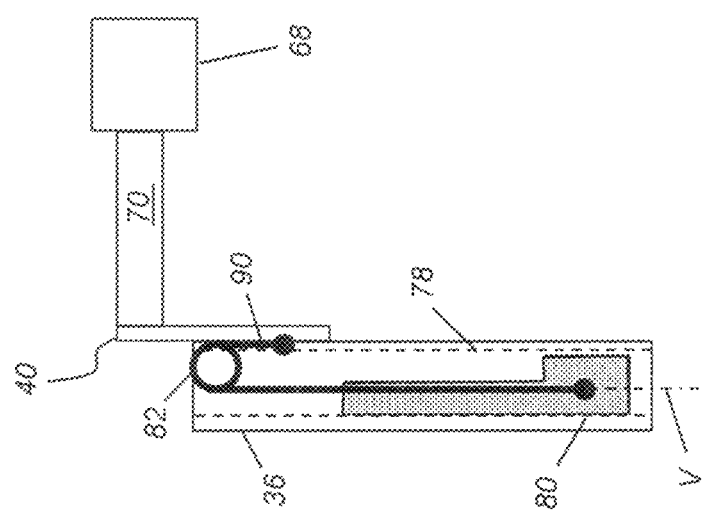
Figure 3D:
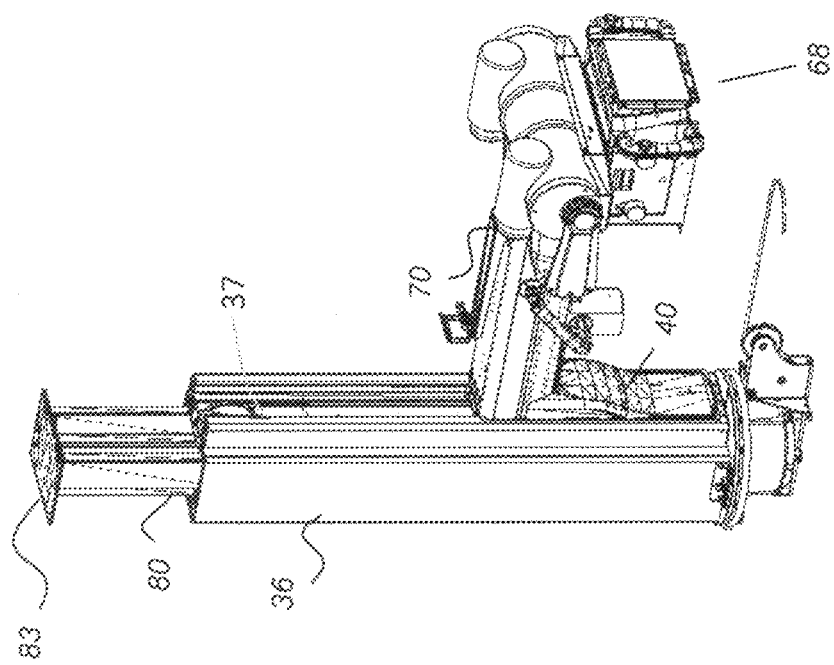
FIGS. 3C and 3D are perspective views that show the boom in the raised and lowered positions, respectively, and show a cap on the counterweight extending above a top of the movable upper section.

FIGS. 3A-3D show the movable upper section 36 in isolation together with boom 70, x-ray tube head 68 and a counterweight 80 used to assist in lowering and raising the boom 70 and x-ray tube head 68. As shown in FIGS. 3B and 3D, with boom 70 lowered, counterweight 80 can extend through shaft 78 in the movable upper section 36 above the top edge of the movable upper section 36. An optional cap 83 may be provided to cover the opening of shaft 78 at the top of movable section 36. FIG. 3B shows a shaft height H2, in an embodiment in which shaft 78 extends fully through movable section 36. The counterweight 80 is configured to balance the weight of boom 70 and x-ray tube head 68 by providing a boom transport apparatus 40 for attaching the boom 70 to a track 37 in the movable upper section 36. In addition, the counterweight 80 is coupled to the boom transport apparatus 40 using a cable 90 attached to the boom transport apparatus 40 and to the counterweight 80, which cable 90 is also looped around a pulley 82 attached to the movable upper section 36.

It is beneficial to allow the fullest possible range of vertical heights for the x-ray source in a portable system, from above shoulder height of the imaging technician (FIG. 2A) to relatively low elevations, such as might be beneficial for imaging the foot or ankle of a patient (FIG. 2B). Applicants have noted that during the operations of extending and retracting the boom 70 there can be an improvement in the operation. For example, reducing noise, so as to not interfere or adversely affect the comfort of the patient and medical technician or improving smoothness of the operation so as to improve the usability and ease of comfort of the medical technician.

Applicants have developed a new cap feature that is improved over the cap 83 to improve the operation of the mobile radiographic apparatus. One benefit is to eliminate/reduce noise which may occur during the extending and retracting of the movable upper section 36. The vertical column 30 and the components employed to extend/retract the column have many contact points that slide against and contact each other during operation. Applicants' cap and nest feature, as described herein, mitigates undesirable noise issues.

Figure 3C:
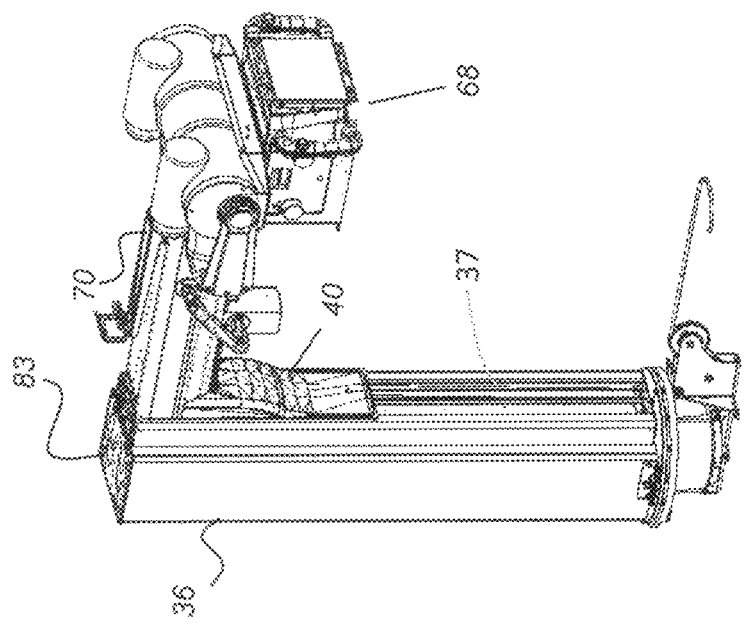
Figure 4:
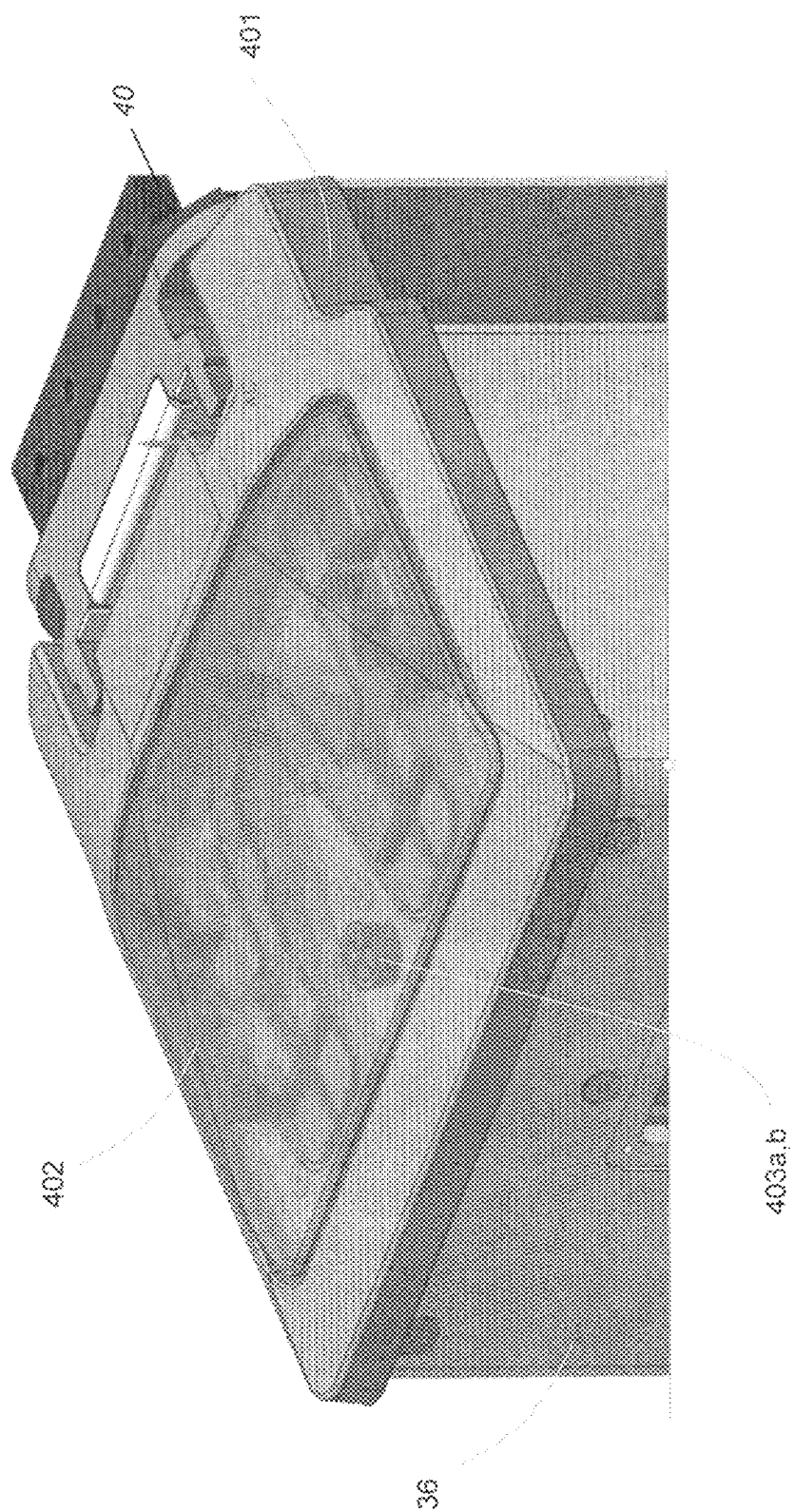
FIG. 4 shows a new cap feature in transparent form in a nest on a top portion of the movable upper section of the vertical column.
Figure 5:
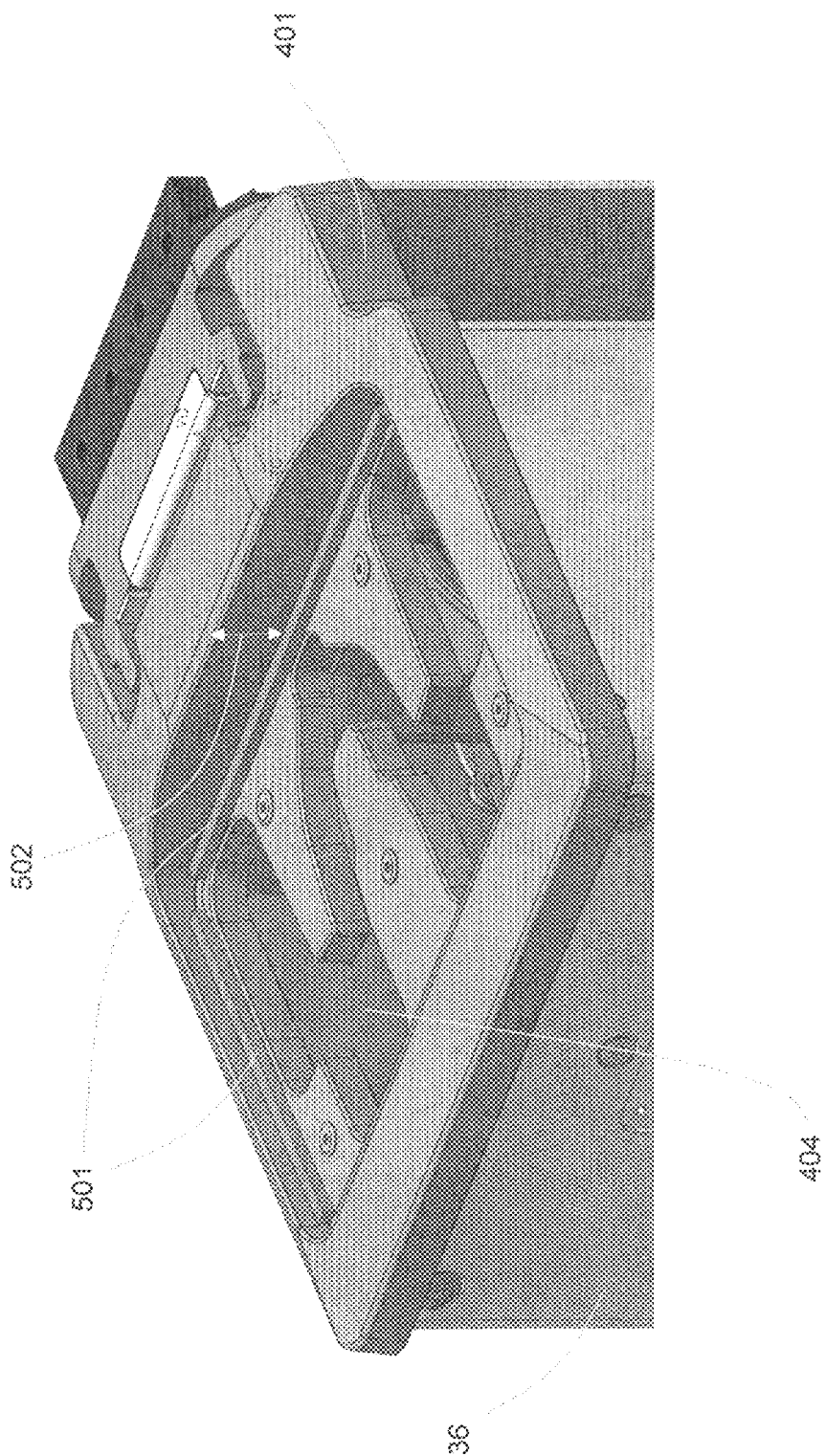
FIG. 5 shows a top of the movable section of the vertical column wherein the cap is removed to illustrate the nest, an opening in the nest for the counterweight, and padding in the nest configured to contact the cap.

The cap feature is located at the top of the movable section 36 of the vertical column 30. It is employed when the counterweight 80 within the movable upper section 36 is extended and retracted. The location of the cap and its nest is at position 39 in FIGS. 2A-2B. Referring to FIG. 4, the nest 401 is attached to a top end of the movable upper section 36 and is configured to receive a cap 402, shown in transparent form, seated in a recessed portion 502 (FIG. 5) of the nest 401. A magnet 403a (FIG. 7), attached to the cap 402, and a magnet 403b (FIG. 7), attached to the nest 402, are aligned such that the cap 402 readily seats into the nest 401 by a force of magnetic attraction when the cap 402 and the nest 401 are brought in adjacent proximity to each other, i.e., when the counterweight 80 is retracted from a position above a top of the movable upper section 36 (e.g., as shown in FIG. 3D) into the movable upper section 36 (e.g., as shown in FIG. 3C). Referring to FIG. 5, wherein the cap 402 is removed, for ease of description, a padding 501 may be disposed around the periphery of the recessed portion 502 of the nest 401 (see also FIG. 8). The relatively soft padding 501 is configured to contact the cap 402 when the cap is lowered onto the nest during retraction of the counterweight 80 into the movable upper section 36. The nest 401 includes an opening 404 at the bottom of its recessed portion 502, which opening 404 is shaped to match a cross-section of the counterweight 80 to allow the counterweight 80 to travel through the opening 404 of the nest 401.

Figure 6:
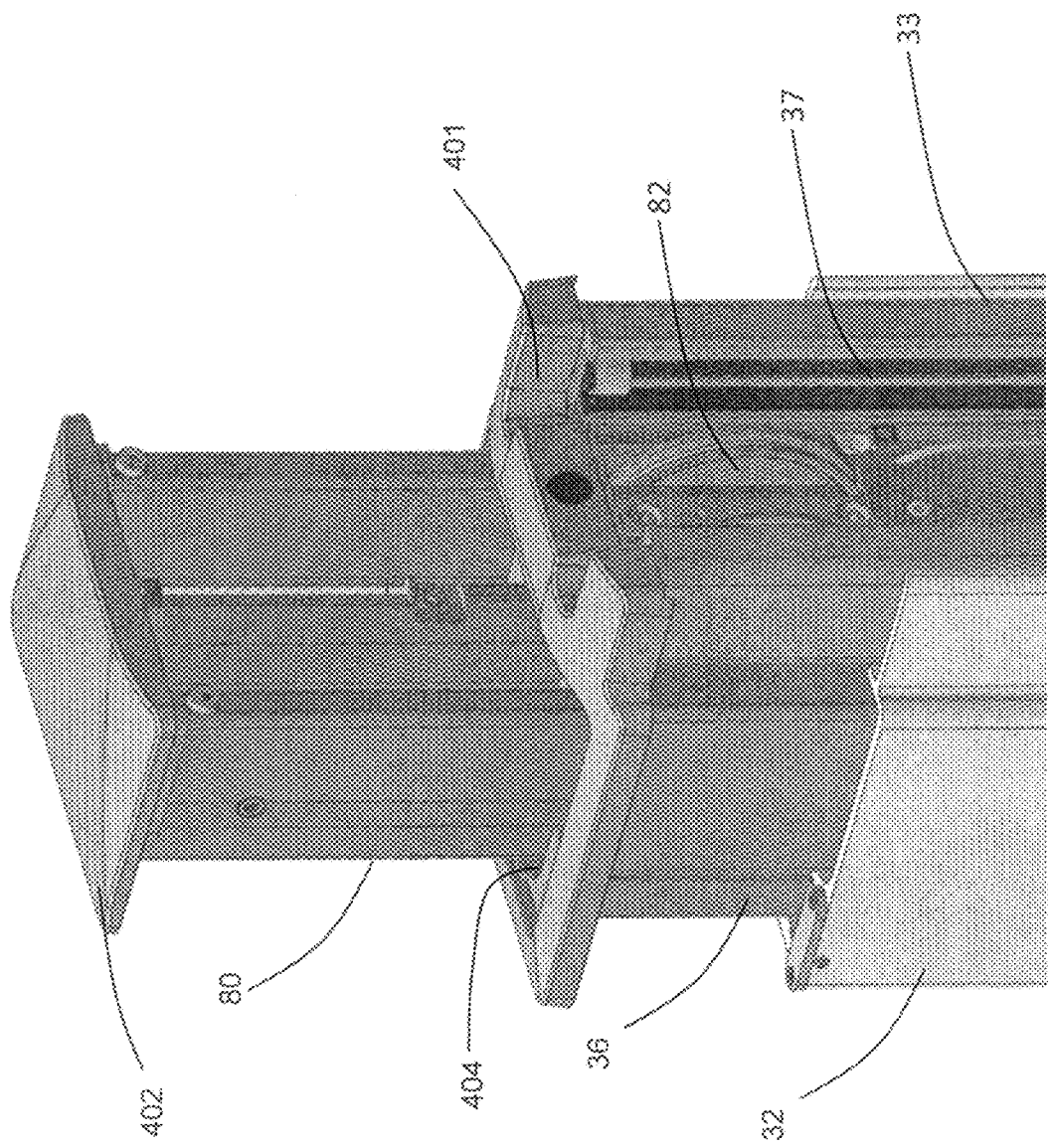
FIG. 6 shows the counterweight extending through the nest.
Figure 7:
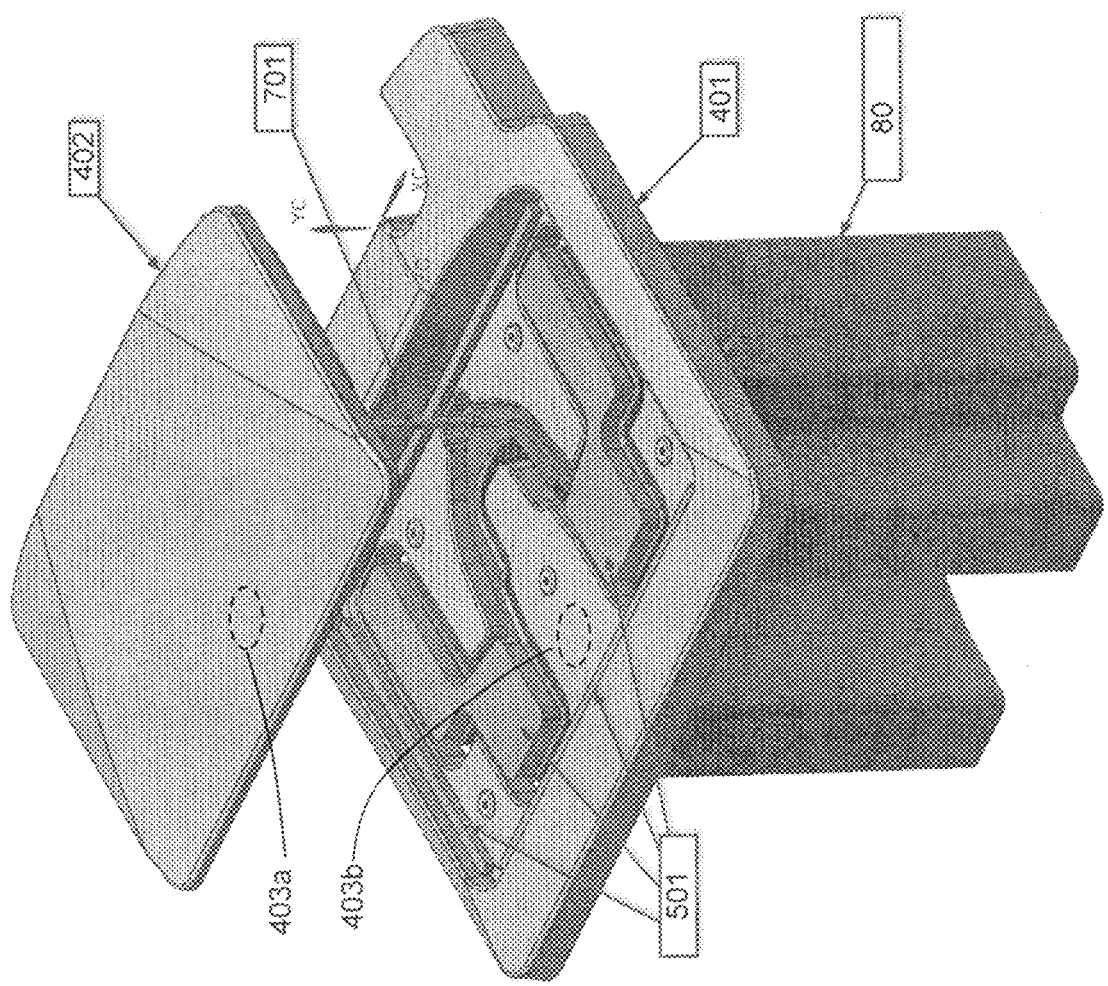
FIG. 7 is an exploded view of the new cap, nest, padding on a top surface of the counterweight, and padding in the nest.

Referring to FIG. 6, the counterweight 80 is shown extending through the opening 404 of the nest 401. The counterweight 80 reaches the position as shown in FIG. 6 by traveling upward through the shaft 78 in the movable upper section 36 when a user of the mobile radiography apparatus 20 lowers the boom 70 (not shown in FIG. 6) along track 37 to a position such as shown in FIG. 2B, which corresponds to a counterweight position such as illustrated in FIGS. 3B and 6. In this position, the cable 90 (not shown in FIG. 6) is extended downward at one end by its attachment to the boom transport apparatus 40 (FIG. 3B), while the other end of the cable 90, attached to the counterweight 80 and looped around pulley 82, raises the counterweight 80 through the opening 404 and above a top end of the movable upper section 36. The counterweight 80 makes contact with the cap 402 and lifts the cap 402 off the nest 401 to the position as shown in FIG. 6. To mitigate the noise associated with the contact of the counterweight 80 with the cap 402, a polyurethane padding, such as PORON®, may be disposed at various (preferably all) contact surfaces as between the counterweight 80 and the cap 402. In one embodiment, the polyurethane padding 501 is placed on a top surface of the upper end of the counterweight 80 as shown in the exploded view of FIG. 7. FIG. 7 also illustrates the polyurethane padding 501 placed around the periphery of the recessed portion 502 of the nest 401. FIG. 7 also illustrates an optional tether 701 that may be attached at one end to the nest 401 or to the counterweight 80, and another end to the cap 402, to prevent the cap 402 from being dropped, such as by sliding off the top of the counterweight 80.

Figure 8:
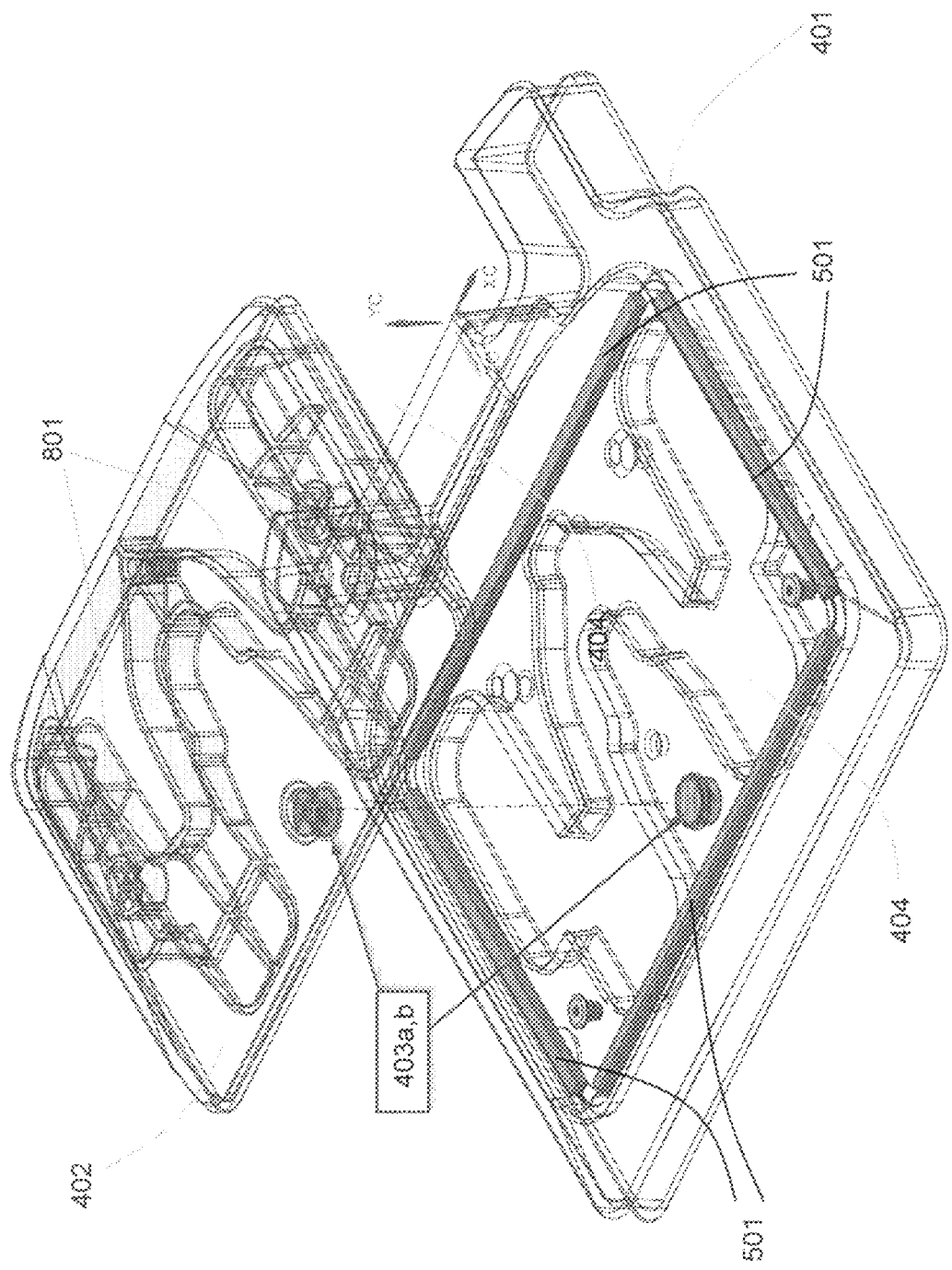
FIG. 8 is a transparent view illustrating padding in the nest, and magnets in the cap and the nest and their alignment to properly position the cap.

To further mitigate noise associated with loose fitting parts during transit, magnets 403a,b, respectively, have been incorporated in the cap 402 and its nest 401 to hold the cap 402 firmly against padding 501 in the nest 401 during transport. The magnetic force between the two magnets 403a,b has been selected to ensure that the magnetic force does not damage components but yet provide sufficient force to stabilize the cap 402 on the nest 401. With reference to FIG. 8, which shows the nest 401 and the cap 402 in transparent form for ease of description, extensions 801, formed on a bottom side of the cap 402, are shaped similarly as the opening 404 through the nest 401, so as to fit therein. The magnets 403a,b are aligned to kinematically attract and position the extensions 801 in the opening 404, so as to continuously engage the cap 402 against the counterweight 80 in the same location, thereby minimizing the possibility of scraping during engagement of the cap 402 to the counterweight 80 and so that the cap 402 is stably positioned in the nest 401 during transport of the mobile radiography apparatus 20.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A mobile radiography system comprising:
   a transport frame having wheels attached thereto for rollably transporting the system;
   a telescoping vertical column mounted on the transport frame, the vertical column comprising a stationary vertical base section mounted on the transport frame, and a vertically movable upper section coupled to the base section and movable relative to the base section;
   a nest attached to a top of the movable upper section, the nest comprising a magnet; and
   a cap comprising a magnet, the cap held against the nest by the magnet of the cap and the magnet of the nest, wherein the cap is configured to be displaced from the nest when a counterweight is extended past the top of the movable upper section, and wherein the cap is configured to be replaced in the nest when the counterweight is retracted into the movable upper section.

2. The system of claim 1, wherein the nest comprises a padded nest portion positioned such that the cap abuts the padded nest portion when the cap is placed in the nest.

3. The system of claim 2, wherein the nest comprises an opening for the counterweight to pass therethrough to displace the cap from the nest while the nest remains attached to the top of the movable upper section.

4. The system of claim 1, wherein the counterweight comprises a padded counterweight portion on a top surface of the counterweight such that the cap abuts the padded counterweight portion when the cap is lifted off the nest by the counterweight.

5. A mobile radiography system comprising:
   a transport frame having wheels attached thereto for rollably transporting the system;
   a telescoping vertical column mounted on the transport frame, the vertical column comprising a stationary vertical base section mounted on the transport frame, and a vertically movable upper section coupled to the base section and movable vertically relative to the base section;
   a counterweight disposed within the movable upper section;
   a nest attached to a top of the movable upper section; and a cap seated in the nest, wherein the cap is configured to be displaced from the nest when a counterweight is extended past the top of the movable upper section, and wherein the cap is configured to be replaced in the nest when the counterweight is retracted into the movable upper section.

6. The system of claim 5, further comprising a first magnet attached to the cap and a second magnet attached to the nest to hold the cap against the nest when the cap and the nest are adjacent.

7. The system of claim 6, wherein the magnets are selected such that their magnetic attractive force allows the cap to be displaced from the nest by the counterweight.

8. The system of claim 5, wherein the nest comprises an opening shaped to match a cross section of the counterweight to allow the counterweight to travel through the opening in the nest.

9. The system of claim 5, wherein the nest comprises padding that contacts the cap when the cap is placed in the nest.

10. The system of claim 9, wherein the counterweight comprises padding that contacts the cap when the counterweight displaces the cap.

11. A mobile radiography cart comprising:
a transport frame having wheels attached thereto for rollably transporting the transport frame;
a telescoping vertical column mounted on the transport frame, the vertical column comprising a stationary vertical base section mounted on the transport frame, and a vertically movable upper section coupled to the base section and movable relative to the base section;
a nest attached to a top of the movable upper section, the nest comprising nest padding; and
a cap configured to seat in the nest against the nest padding;
wherein the cap is configured to be displaced from the nest and replaced in the nest against the nest padding.

12. The cart of claim 11, further comprising a counterweight in the vertically movable upper section, wherein the nest comprises an opening for the counterweight to pass therethrough to displace the cap from the nest while the nest remains attached to the top of the movable upper section.

13. The cart of claim 12, wherein the counterweight comprises a counterweight padding on a top surface of the counterweight such that the cap abuts the counterweight padding when the cap is displaced by the counterweight.

14. The cart of claim 13, wherein the counterweight is configured to retract into the movable upper section to replace the cap in the nest against the nest padding.

15. The cart of claim 13, further comprising a first magnet in the nest and a second magnet in the cap, the cap held in the nest against the nest padding by a magnetic force.

16. The cart of claim 15, wherein the nest comprises a recessed portion, the nest padding is disposed in the recessed portion, and wherein the cap is configured to seat in the recessed portion against the nest padding.

* * * * *